United States Patent [19]

Kristinsson

[11] Patent Number: 4,758,778
[45] Date of Patent: Jul. 19, 1988

[54] METHOD AND AN APPARATUS FOR DETERMINING THE DEGREE OF FRESHNESS OF PIECES OF FOOD

[75] Inventor: Björn Kristinsson, Reykjavik, Iceland

[73] Assignee: Rafagnataekni (Electronics), Reykjavik, Iceland

[21] Appl. No.: 815,588

[22] Filed: Jan. 2, 1986

[30] Foreign Application Priority Data

Jan. 2, 1985 [DK] Denmark .................................. 23/85

[51] Int. Cl.⁴ .......................................... G01R 27/02
[52] U.S. Cl. .................... 324/65 R; 209/571; 209/701; 324/71.1; 324/149
[58] Field of Search .................... 324/65 R, 65 P, 539, 324/545, 552, 571, 540, 701, 917, 149, 71.1; 198/404, 720, 370

[56] References Cited

U.S. PATENT DOCUMENTS

| | | | |
|---|---|---|---|
| 2,937,739 | 5/1960 | Levy | 209/917 X |
| 3,320,946 | 5/1967 | Dethloff et al. | 324/61 R X |
| 3,665,302 | 5/1972 | Lees et al. | 324/71.1 X |
| 4,082,188 | 4/1978 | Grimmell et al. | 250/223 R X |
| 4,214,663 | 7/1980 | Schopp et al. | 209/552 |
| 4,320,841 | 3/1982 | Gordon et al. | 209/552 |

FOREIGN PATENT DOCUMENTS

| | | |
|---|---|---|
| 370270 | 11/1937 | Canada . |
| 742885 | 9/1966 | Canada . |
| 74463 | 7/1962 | Denmark . |
| 421308 | 12/1966 | Denmark . |
| 1084495 | 6/1956 | Fed. Rep. of Germany . |
| 92107 | 5/1958 | Netherlands . |
| 1262749 | 2/1972 | United Kingdom . |
| 1287190 | 8/1972 | United Kingdom . |

OTHER PUBLICATIONS

European Search Report-EP 85 116669.

Primary Examiner—Reinhard J. Eisenzopf
Assistant Examiner—Robert W. Mueller
Attorney, Agent, or Firm—Merchant, Gould, Smith, Edell, Welter & Schmidt

[57] ABSTRACT

By a method of and an apparatus for determining the degree of freshness of fish or other pieces of meat a pair of electrodes of an electrode assembly are brought into contact with the pieces of food, and the degree of freshness is determined electrically by determining the phase angle of the impedance which the tissue of the piece of food in question represents by inducing an alternating current into the tissue of the piece of food and by determining the delay of the voltage produced by the current in relation to the current. The peices of food are successively moved along a first path of movement across a supporting surface, in which a first electrode assembly is mounted for measuring the degree of freshness of the pieces of food at the first side, whereafter the pieces of food are successively turned upside down and moved along a weighing unit and further along a second path of movement across a supporting surface, in which a second electrode assembly is mounted for measuring the degree of freshness of the other side of the piece of food. On the basis of the measurement of the degree of freshness and the weight of the piece of food in question, the pieces of food are sorted by means of sorting means, which bring the pieces of food to respective containers. The sorting apparatus for carrying out the method comprises a first and a second supporting surface along which two measuring assemblies are mounted, a weighing unit, means for turning the pieces of food upside down and sorting means for sorting the pieces of food into respective containers on the basis of the results determined by means of the electrode assemblies and by means of the weighing unit.

15 Claims, 4 Drawing Sheets

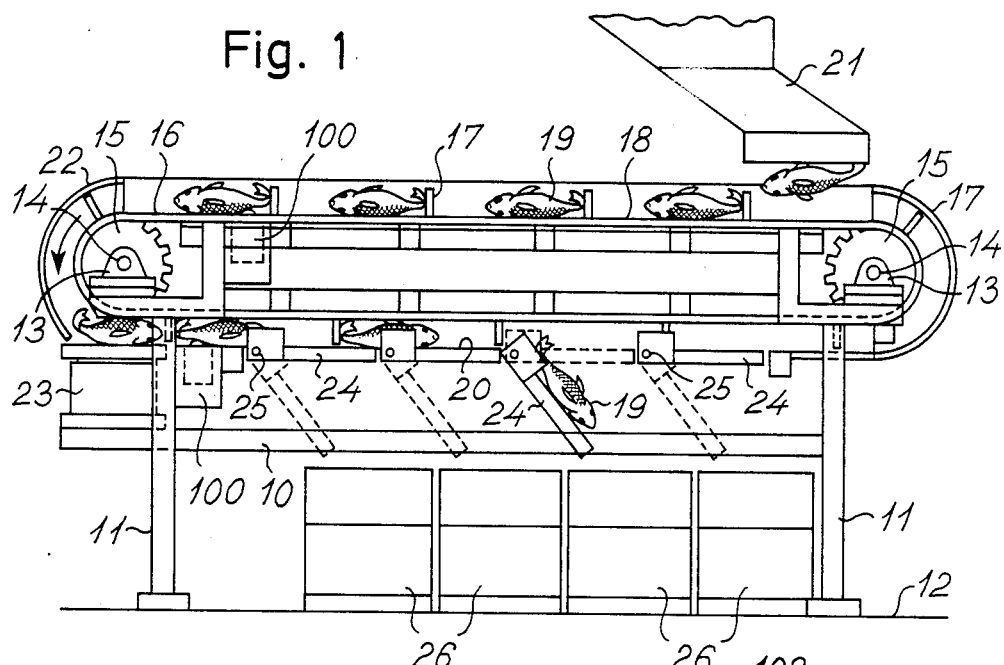
Fig. 1
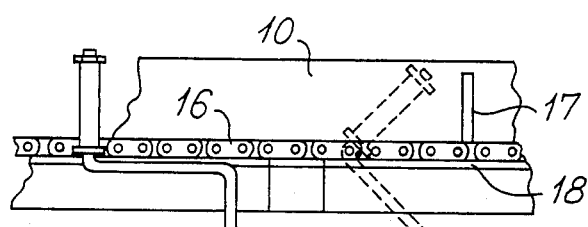
Fig. 3
Fig. 2
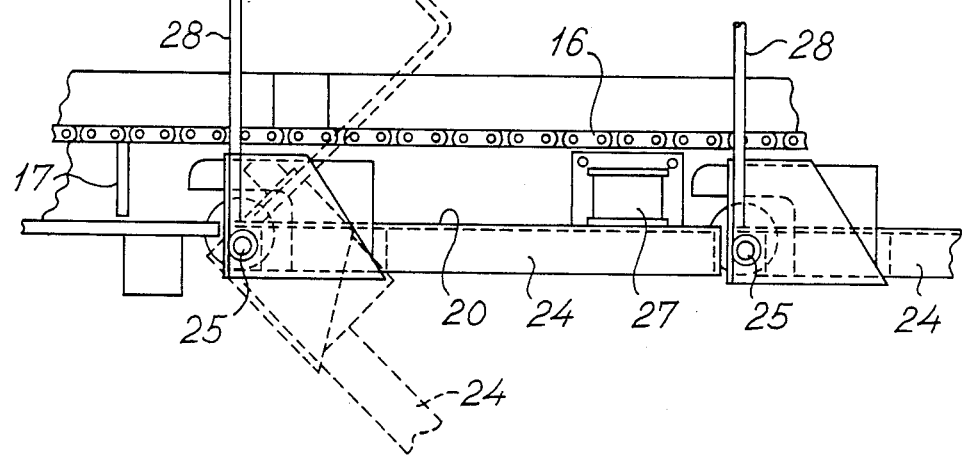

METHOD AND AN APPARATUS FOR DETERMINING THE DEGREE OF FRESHNESS OF PIECES OF FOOD

BACKGROUND OF THE INVENTION

The present invention relates to a method of determining the degree of freshness of pieces of food such as fish, fillets of fish with or without skin, and other kinds of meat.

In evaluating the quality and the degree of freshness of meat and meat products, Including fish and fish products, it has up till now been necessary to make a more or less subjective evaluation based on the colour and the smell of the product. However, it would be desirable to be able to make a more objective evaluation or measurement of the degree of freshness.

During bacteriological decomposition of fish and other meat products various gases such as trimethylamine and other volatile bases are developed, and a "quality index" for fish based on a chemical determination of such developed gases has been proposed. Furthermore, the British patent specifications Nos. 1,262,749 and 1,287,190 disclose an apparatus for electrically determining the degree of freshness or the condition of food products or the bacteriological decomposition of such products. The development of this known apparatus is based on a study showning that the dielectrical characteristics of fish meat change in a regular manner with the time period which has lapsed after killing of the fish, when the meat is kept at a certain temperature. A report concerning this study which was made at "Torry Research Station", Aberdeen, and made by A. C. Jason and A. Lees, was published in the British "Department of Trade and Industry" in April, 1971.

This known apparatus is intended for measurement of randomly selected test samples, the apparatus comprising an abutment surface having electrical electrodes embedded therein. The freshness of a fish is measured by contacting the abutment surface of the apparatus with one side of the fish, and the result of the measurement may then be read from a digital display or another kind of display unit. Tests have shown that the measuring results obtained by means of this known apparatus are substantially independent of the position of which the measurement is carried out provided that the abutment surface of the apparatus is placed adjacent to the median line of the fish and not too close to the head or tail of the fish, it is therefore proposed to use the known apparatus for making a single measurement for each fish at a closely defined position adjacent to the median line of the fish.

SUMMARY OF THE INVENTION

The present invention provides a method of the above type permitting a quick and accurate electrical measurement of rather large quantities of pieces of food such as fish or other pieces of meat so that the measurements made may in practice be used as a basis for sorting the fish or pieces of food.

The method according to the invention copmrises successively moving said pieces of food along a path of movement past a first set of electrodes while one side of each piece of food is kept in contact with the electrodes, carrying out a plurality of successive measurements by means of the electrodes on each piece of food passing the electrodes, and determining the degree of freshness of each piece of food on the basis of such measurements. The path of movement along which the pieces of food or the fish are moved and in which he said electrodes are arranged may, for example, be a path for transporting the pieces of food from one processing station or processing apparatus (such as sorting, cleaning, cutting, salting), or the path of movement may constitute part of such processing apparatus. Preferably a rather high number of measurements are made while each piece of food or each fish is passing the set of electrodes, and the measuring signals generated may be transmitted to an electronic calculating or control device or unit such as a microcomputer, which may be programmed so as to register the measurements of freshness for each single piece of food and possibly for sorting the pieces of food on the basis of these measuring results, for example by diverting pieces of food which are judged to be not sufficiently fresh, from the path of movement. By such registering and/or judging on the basis of measuring results it is normally advantageous to disregard measuring results from the rim zones of the pieces of food, as the measuring results from these areas may be less reliable as mentioned above.

The degree of freshness of a piece of food may vary from one area to another of the same piece of food. This may, for example, be true for fish which have been stored without being sufficiently covered by ice so that some areas of a fish are covered by ice while other areas of the same fish have been uncovered and possibly exposed to the sun. If desired, the electronic control unit may be programmed so as to discard a piece of food if one or any other predetermined maximum number of the measurements made on this piece of food does not correspond to a predetermined degree of freshness. However, in a preferred embodiment of the method according to the invention, the degree of freshness of each single piece of food is determined by averaging the plurality of values of measurements obtained. However, as mentioned above, the measurements carried out at the rim zones are normally disregarded.

As indicated above, the degree of freshness of a piece of food may vary from one area to another on the same side of the piece of food, but the degree of freshness may vary to an even higher degree from one side of the piece of food to the other. If, for example, the pieces of food are fish which have been stored without being sufficiently covered by ice, the upper side of a fish may be uncovered and possibly exposed to the sun, while the lower side may be supported on a layer of ice. In order to pay regard to such situations each piece of food, which has been moved past the set of electrodes, may be turned upside down and moved past and brought into contact with a second set of electrodes for measuring the degree of freshness of the other side of this piece of food. The electronic control device or unit may then be programmed so as to also register the measuring results from this other side of the piece of food and possibly for discarding such pieces of food if the degree of freshness of the said other side thereof is not found to be satisfactory.

In a preferred embodiment of the method according to the invention the pieces of food for which the freshness is being determined are moved over a weighing device positioned in the path of movement and the pieces of food may then be sorted on the basis of their degree of freshness as well as their weight. In a manner known per se the pieces of food may be divided into groups each comprising pieces of food having a weight within predetermined limits, and the pieces of food having a degree of freshness which does not fulfill predetermined criteria may be routed to a special group irrespective of their weight. It should be understood that the sorting may be based not only on the degree of freshness, but also on other criteria, such as length or shape, if desired.

The type of the set of electrodes used may be chosen dependent on the type of food in question. As an example, the set of electrodes may comprise a pH-electrode when the pieces of food are meat from mammals. When the said pieces of food are fish or fillets of fish with skin it is preferred to base the determination of the degree of freshness on measurements of a species selected from the group consisting of the electrical impedance, the phase angle, the resistance, the reactance, the sharpness of resonance, the time constant, and combinations of such species of part of each piece of food. The measurement of the species, e.g. the electrical impedance or any other species related to the electrical impedance may be carried out by comparing a voltage or current supplied to an area of the piece of food with the response provided in the form of a current or voltage response for determining the electrical impedance or the measuring values in question in accordance with well-known physical principles including Ohm's law, etc. Dependent on the measuring values to be determined and dependent on whether it is desired to cause polarisation of the electrodes in contact with the said area of the piece of food in question, alternating or constant voltages or currents or combinations of alternating and constant voltages and currents may be used.

In accordance with a preferred embodiment of the method according to the invention, the determination of the degree of freshness of each piece of food is carried out by means of four electrodes, a first pair of which is used as emitter electrodes, and a second pair of which is used as receiver electrodes, by supplying an alternating current to said pair of emitter electrodes, by measuring the alternating voltage generated over the receiver electrodes, and by measuring the phase angle between the current supplied and the voltage generated. By using this embodiment of the method according to the invention for determining the degree of freshness of fish, problems due to polarization of the issue in the part of the fish contacted by the electrodes are eliminated.

The invention also relates to an apparatus for determining the degree of freshness of pieces of food, such as fish and other kinds of meat, said apparatus comprising a supporting surface, moving means for successively moving the pieces of food along a path of movement defined by said supporting surface, measuring means positioned along the path of movement for measuring characteristics of the pieces of food, and sorting means for sorting the pieces of food on the basis of the measurements carried out by the measuring means, said measuring means comprising a set of electrodes positioned at the supporting surface along the path of movement and adapted to determine the degree of freshness of the pieces of food. Such apparatus may be used for sorting pieces of food on the basis of their degree of freshness and possibly also on the basis of one or more other measurable characteristics, such as weight, length, shape, colour, type, etc. as explained above.

In order to permit measurement of the degree of freshness on both sides of the pieces of food, the measuring means of the apparatus according to the invention preferably further comprise a further set of electrodes for determining the degree of freshness of the pieces of food and positioned at the supporting surface along the path of movement and turning means for turning upside-down passing pieces of food, the turning means being arranged between the two sets of electrodes. The path of movement may e.g. comprise a pair of aligned path lengths, and the turning means may e.g. comprise a pivotally mounted turning flap or a turning wheel.

In order to obtain reliable measuring results in measuring the degree of freshness of the pieces of food it is essential to ensure good contact between the said set of electrodes positioned in the path of movement and the pieces of food passing these electrodes. This may be obtained e.g. by providing an upwardly convexly curved shape of the supporting surface defining the path of movement at least at the position or positions at which the set of electrodes is arrangned. A particularly good contact may be ensured by embedding at least one of said sets of electrodes in a raised part of the supporting surface so as to support a major part of the weight of a piece of food passing such raised portion by the raised part.

In the above described embodiment of the apparatus according to the invention wherein the measuring means comprise two sets of electrodes for determining the degree of freshness on respective opposite sides of each piece of food, the supporting surface may comprise vertically spaced upper and lower substantially horizontally extending surface parts, and the moving means may comprise an endless conveyor belt, which is provided with carriers and has its upper and lower paths extending along said upper and lower surface parts, respectively. In this embodiment of the apparatus according to the invention the total length of the apparatus may be made smaller than the total length of a corresponding apparatus in which the path of movement comprises two aligned path lengths. Furthermore, the pieces of food may be turned upside down by the conveyor belt when they pass from one of the vertically spaced surface parts to the other. This means that the use of a turning flap, a turning wheel or another special device for turning the pieces of food is unnecessary.

As mentioned above the sorting of the pieces of food may be carried out not only on the basis of their degree of freshness, but also on the basis of one or more further criteria, such as the weight, length, shape, colour and-/or the type of the pieces of food. Normally, fish are sorted with regard to their size on the basis of their weight. In order to permit sorting of the pieces of food or the fish on the basis of the degree of freshness as well as the weight, the measuring means may further comprise a weighing device and the apparatus may further comprise diverting means, which may e.g. be in the form of trap doors and may be activated in response to measuring signals received from the measuring means, and which may be arranged along the path of movement downstream of the set of electrodes and of the weighing unit.

In the apparatus according to the invention, the sorting may be carried out based directly on the measuring signals generated by the measuring means. Thus, the measuring signals generated by the set of electrodes may directly, but possibly via an amplifier means or a relay coupling, actuate the sorting means. The preferred embodiment of the apparatus according to the invention further comprises a central control device or unit adapted to control the operation of the apparatus and connected to the measuring means for receiving measuring signals therefrom, and to the moving means and to the diverting means for controlling the operation thereof. The central control device or unit may advantageously include a microcomputer or another similar electronic control device.

As described above, the degree of freshness of a piece of food may be based on the measurement of the electrical impedance of part of a piece of food. Consequently, the apparatus may comprise an electronic measuring amplifier means, which is connected to the set of electrodes, for measuring a species selected from the group consisting of the electrical impedance, the phase angle, the resistance, the reactance, the sharpness of resonance, the time constant and combinations of such species of the part of the piece of foof which is in contact with the set of electrodes.

In order to eliminate the above problems relating to polarization of the electrodes contacting the tissue of a piece of food, the set of electrodes or each set of electrodes preferably comprises four electrodes, a first pair of which constitutes emitter electrodes, and a second pair of which constitutes receiver electrodes, and the measuring amplifier means preferably comprises an oscillator and is adapted to supply an alternating current to the emitter electrodes at a frequency determined by the oscillator, to measure the alternating voltage generated by the receiver electrodes, and to determine the phase angle between the current supplied and the voltage generated.

The determination of the phase angle between the current and the voltage may be carried out in any appropriate manner desired. Thus, the voltage and the current may be supplied to respective half-wave rectifier circuits or peak value detecting circuits, and the time difference between the signals generated by these rectifier and detecting circuits may be compared by means of suitable discriminating or gate circuits. In order to obtain the highest possible accuracy and reliability of the measurement and in order to increase the rate of measurement also, the measuring amplifier means preferably comprises a double-sided phase comparison circuit for determining the phase angle between current and voltage in both half-periods in contrast to the above described embodiment comprising half-wave rectifier circuits, in which the phase angle is determined on the basis of one half-period only.

BRIEF DESCRIPTION OF THE DRAWINGS

The invention will now be further described with reference to the drawings, wherein FIG. 1 is a side view of an embodiment of a sorting apparatus according to the invention, FIG. 2 is an enlarged fragmentary side view of the apparatus shown in FIG. 1, FIG. 3 is a perspective view of an electrode unit contained in the sorting apparatus shown in FIG. 1.

DETAILED DESCRIPTION OF THE INVENTION

Figure 5:
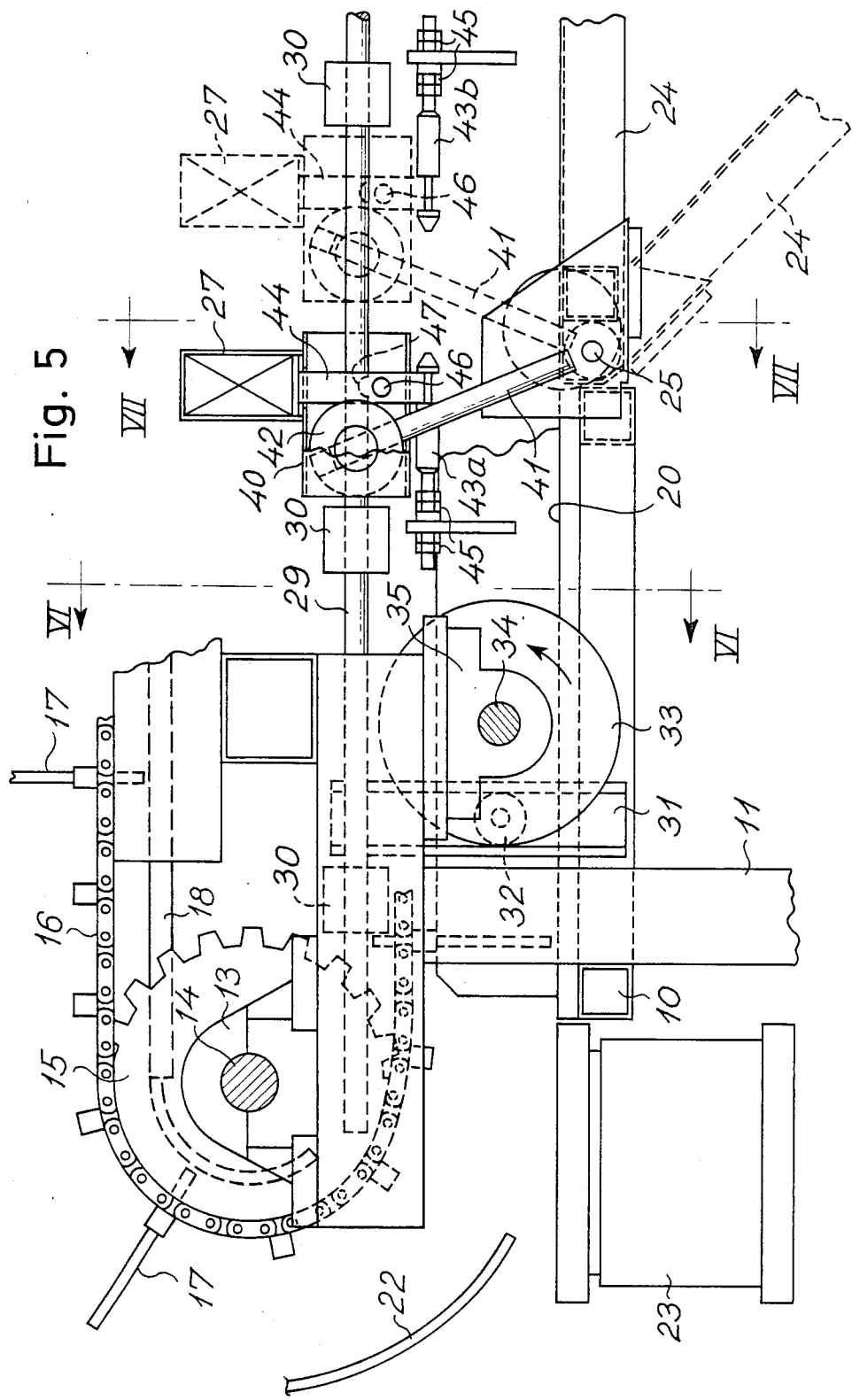
FIG. 5 is a side view of a modified embodiment of the apparatus according to the invention where certain parts have been cut away.

The apparatus as shown in the drawings comprises a frame 10 resting on a supporting surface, such as a floor 12, by means of legs 11. A pair of spaced, substantially horizontally extending, parallel shafts 14 are rotatably arranged in bearing houses 13 which are mounted on the frame 10. A pair of spaced gears or sprockets 15 are mounted on each shaft. Each of a pair of spaced toothed belts or chains 16 is passed around a pair of said gears or sprockets 15 arranged in a common vertical plane and mounted on each one of the shafts 14. Each of a number of carriers 17 extending perpendicularly to the belts or chains 16 is fastened to both of said belts or chains 16 so that each carrier extends upwards from the top surfaces of the upper runs of the belts or chains 16 or downwards from the bottom surfaces of the lower runs of the belts or chains as best shown in FIG. 5. A supporting plate defining an upper path of movement 18 for fish 19 or other pieces of food to be sorted by the apparatus is mounted on the frame 10 between the upper runs of the chains or belts 16 at substantially the same level as these upper runs. Furthermore, a stationary lower path of movement 20 is defined on the frame 10 between the lower runs of the belts or chains 16, but at a slightly lower level than these runs. Fish 19 or other pieces of food to be sorted in the apparatus are supplied to one end (the right hand end in FIG. 1) of the apparatus via a chute 21 or other suitable supply means. These supply means may be operated automatically so that they are adapted to place one fish 19 or piece of food at the time between each pair of succeeding carriers 17 on the upper path of movement 18 as shown in FIG. 1. The supply of fish or pieces of food may also be performed manually, and they may then for example one by one be pushed onto the path of movement from a supply table (not shown) extending at the same level as and transversely to the path of movement and parallel with the carriers 17. When one of the shafts 14 is rotated by means of a driving motor (not shown), the chains 16 with the carriers 17 mounted thereon will push the fish 19 along the upper path of movement 18, and when a fish or piece of food reaches the left hand end of the apparatus as shown in FIG. 1, it is guided by a guide plate 22 formed as an arc of a circle and arranged concentrically with the adjacent sprocket 15, and moved downwards until it is placed on the lower path of movement 20 whereby it has been turned upside down. The carriers 17 will then push the fish or the pieces of food successively along the lower path of movement 20.

The lower path of movement 20 is at least partly defined by the upper supporting surface of a weighing unit 23 and by the upper sides of a number of successively arranged trap doors 24, each of which may be pivoted around a pivot 25 between a substantially horizontal position and a downwardly extending position. A collecting container 26 for receiving a certain sorting category of the fish or pieces of food being sorted, is arranged below each of the trap doors 24, if desired, the containers 26 may be replaced by a conveyor adapted to transport the fish or pieces of food to another processing station such as a filleting machine or another processing apparatus. A solenoid or electromagnet 27 is associated with each of the trap doors 24, and when the solenoid or electromagnet 27 is energized, the associated trap door 24 is maintained in its upper position. The function of the trap doors and, consequently, the sorting of the fish 19 may be controlled, by controlling the supply of energizing current to the solenoids, in synchronism with the movement of the chains 16 and the carriers 17 mounted thereon and in response to measuring signals generated partly by means of two electrode units 100 for determining the degree of freshness of the fish or pieces of food and partly by the weighing unit 23, which permits sorting of the fish 19 in weight categories. The electrode units 100 will be described in greater detail with reference to FIG. 3. One of these electrode units 100 is arranged in the upper path of movement 18 while the other electrode unit is arranged in the lower path of movement between the weighting unit 23 and the adjacent trap door 24. Each of the electrode units 100 is mounted so that its electrodes are embedded in and extend slightly upwards from the responsive path of movement. As will be described in greater detail below, the trap doors 24 may e.g. be controlled by an electronic control device or unit so that fish 19 which—based on measurements carried out by the electrode units 100—are deemed not to be sufficiently fresh and therefore not suited for human consumption are diverted down into the first one of the collecting containers 26 while those of the fish 19 which are deemed to be sufficiently fresh are divided into predetermined weight categories and passed into corresponding ones of the succeeding containers 26 based on weight measurements made by the weighing unit 23.

When one of the trap doors 24 is actuated or released by the electronic control device or unit switching off the current to the associated solenoid, the piece of food or the fish 19 being supported by or arriving at the trap door will fall from the lower path of movement 20 and down into one of the containers 26. Thereafter the trap door 24 must be moved back to its horizontal position before arrival of the succeeding fish 19.

FIG. 2 shows a possible embodiment of such a returning mechanism for the trap doors. In this embodiment a plurality of spaced pins (not shown in the drawings) are fastened to the chain 16 so as to extend therefrom. Furthermore a crank-like returning member 28 is fastened to each trap door 24 so that when the associated trap door is in its released, downwardly extending position shown by dotted lines in FIG. 2, one of the said pins or studs on the upper path of the chain 16 will engage with the returning member 28 and return the same and the associated trap door 24 to the starting position shown by solid lines in FIG. 2. In this horizontal starting position of the trap door the associated returning member extends substantially vertically, and the studs or pins on the upper path of the chain 16 passing the returning member cause the returning member to swing about its vertical axis out of engagement against a spring bias.

Figure 6:
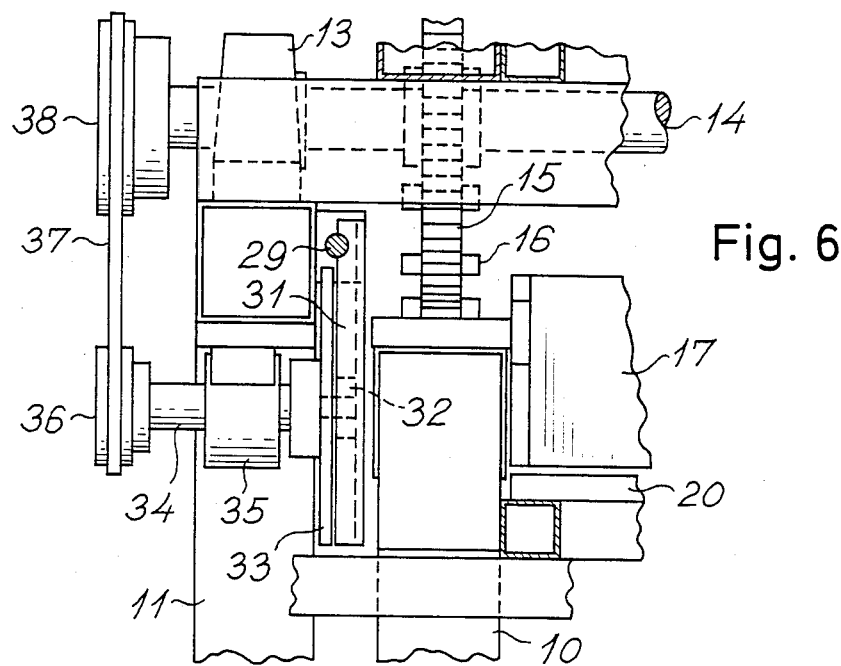
FIG. 6 is part of a sectional view along the line VI—VI in FIG. 5.
Figure 7:
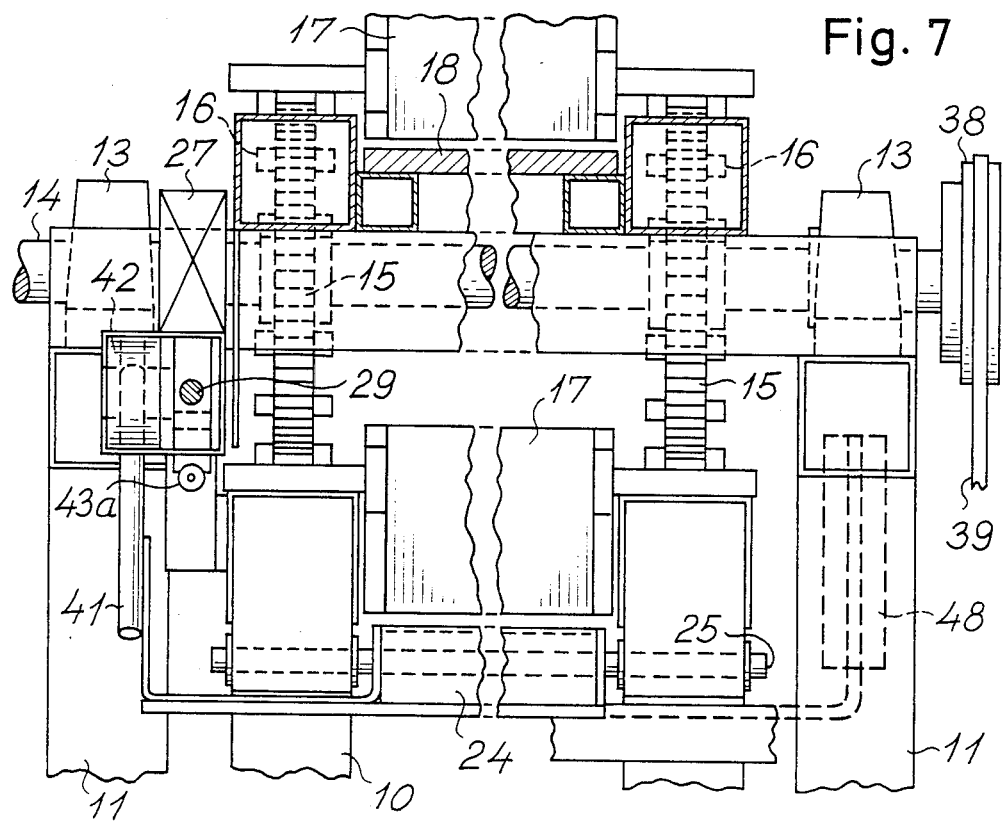
FIG. 7 is a sectional view along the line VII—VII in FIG. 5.

FIGS. 5-7 disclose a modified embodiment of the returning mechanism for the trap doors 24. This embodiment comprises a substantially horizontally extending actuating rod 29 which is mounted in slide bearings 30 fastened on the frame 10 so that the rod 29 may be reciprocated in the longitudinal direction of the apparatus. A guiding channel member 31 is mounted on and extends vertically downwards from the rod 29, and a stud or roller 32 is in engagement with the channel member 31. The stud or roller 32 is eccentrically mounted on and extends from an eccentric disc 33 which is arranged on a shaft 34 extending transversely to the longitudinal direction of the apparatus and rotatably mounted in a bearing 35 which is fastened to the frame 10. A pulley or sprocket 36 is mounted on the free end of a shaft 34 and is in driving connection with a corresponding pulley or sprocket 38 on one end of the shaft 14 by means of a belt or chain 37. A further pulley or sprocket is mounted at the other end of the shaft 14 and may be connected to a driving motor (not shown) by means of a belt or chain 39. When the shaft 14 and the chains 16 are driven by the driving motor via the belt or chain 39 and the pulley or sprocket 38, the shaft 34 and the eccentric disc 33 are also rotated via the belt or chain drive 36–38. Because the stud or roller 32 is in engagement with the channel member 31, rotation of the eccentric disc 33 also causes a reciprocating movement of the actuating rod 29. If the driving members 37 and 39 are in the form of belts they are preferably toothed belts so as to ensure synchronization of the movements of the chains 16 and the trap doors 24.

Each solenoid or electromagnet 27 is mounted on a carriage 40 through which the actuating rod 29 extends so as to be displaceable in relation thereto. An upwardly and rearwardly extending actuating arm 41 is fastened to each of the trap doors 24, and the upper end of the actuating arm 41 is displaceably received in a diametrically extending bore formed in a pivot member 42, which is rotatably mounted in the associated carriage 40. A counterweight 48 mounted on an upwardly extending arm is fastened to the other side of each trap door 24 as best shown in FIG. 7. Each carriage 40 and the solenoid 27 mounted thereon may be displaced between a position which is shown in solid lines in FIG. 5, and in which the associated trap door 24 is held in its closed position, and a position, which is shown in dotted lines in FIG. 5, and in which the trap door 24 is open. In each of these positions the carriage 40 is locked by means of locking devices 43a and 43b, respectively, which are adapted to cooperate with a lower free end of an armature 44 of the solenoid 27.

When the solenoid 27 is not energized, its armature 44 will occupy a lower position in which the free end thereof engages with the locking device 43a so as to retain the solenoid 27 and the associated carriage 40 in this position which may be adjusted by means of adjusting nuts 45, if desired. In this position, which is shown by solid lines in FIG. 5, the corresponding trap door is closed. When the trap door is to be opened, the solenoid 27 is energized causing the armature 44 of the solenoid to move upwards, whereby the free end of the armature is moved out of egagement with the locking device 43a, and at the same time a stud 46 mounted on and extending from the armature 44 is brought into engagement with a corresponding cut-out 47 in the actuating rod 29. When the rod 29 is moved forwards during its reciprocating movement, the carriage 40 and the solenoid 27 mounted thereon will be moved to the right in FIG. 5 to a position indicated by dotted lines, whereby the actuating arm 41 is pivoted clockwise so that the associated trap door 24 is opened. In this position the energizing current supplied to the solenoid 27 is again switched off, whereby the armature 44 falls downwards and the stud 46 is moved out of engagement with the cut-out 47 while the lower end of the armature 44 is moved into engagement with the locking device 43b. When the trap door 24 is to be closed again, the solenoid 27 is energized, whereby the armature 44 is brought out of engagement with the locking device 43b, while the stud 46 is brought into engagement with the cut-out 47, and the rod 29 will move the carriage 40 back to its position shown by solid lines in FIG. 5, whereby the trap door 24 is closed again. It is to be understood that in this manner the trap doors 24 may selectively be opened and closed by controlling the supply of energizing current to the respective solenoids 27, and the opening and closing movements are caused by the constantly reciprocating rod 29.

FIG. 3 discloses in greater detail an electrode assembly 100 like those indicated in FIG. 1. The electrode assembly comprises a housing 101 defining an upper side surface 102, which constitutes part of the upper and the lower paths of movement, designated 18 and 20, respectively, when the assembly is mounted in the sorting apparatus in the manner shown in FIG. 1. From the lower side surface of the housing 101 a multicore cable 103 extends, of which the individual conductors are shown extending from the end of the insulating jacket of the cable. The electrode assembly 100 further comprises two electrode pairs 104 and 105 each including a centre electrode designated 106 and 107, respectively, and preferably made of stainless steel and a graphite electrode designated 108 and 109, respectively, enclosing the corresponding centre electrode 106 and 107, respectively, in relation to which the graphite electrode is insulated.

Figure 4:
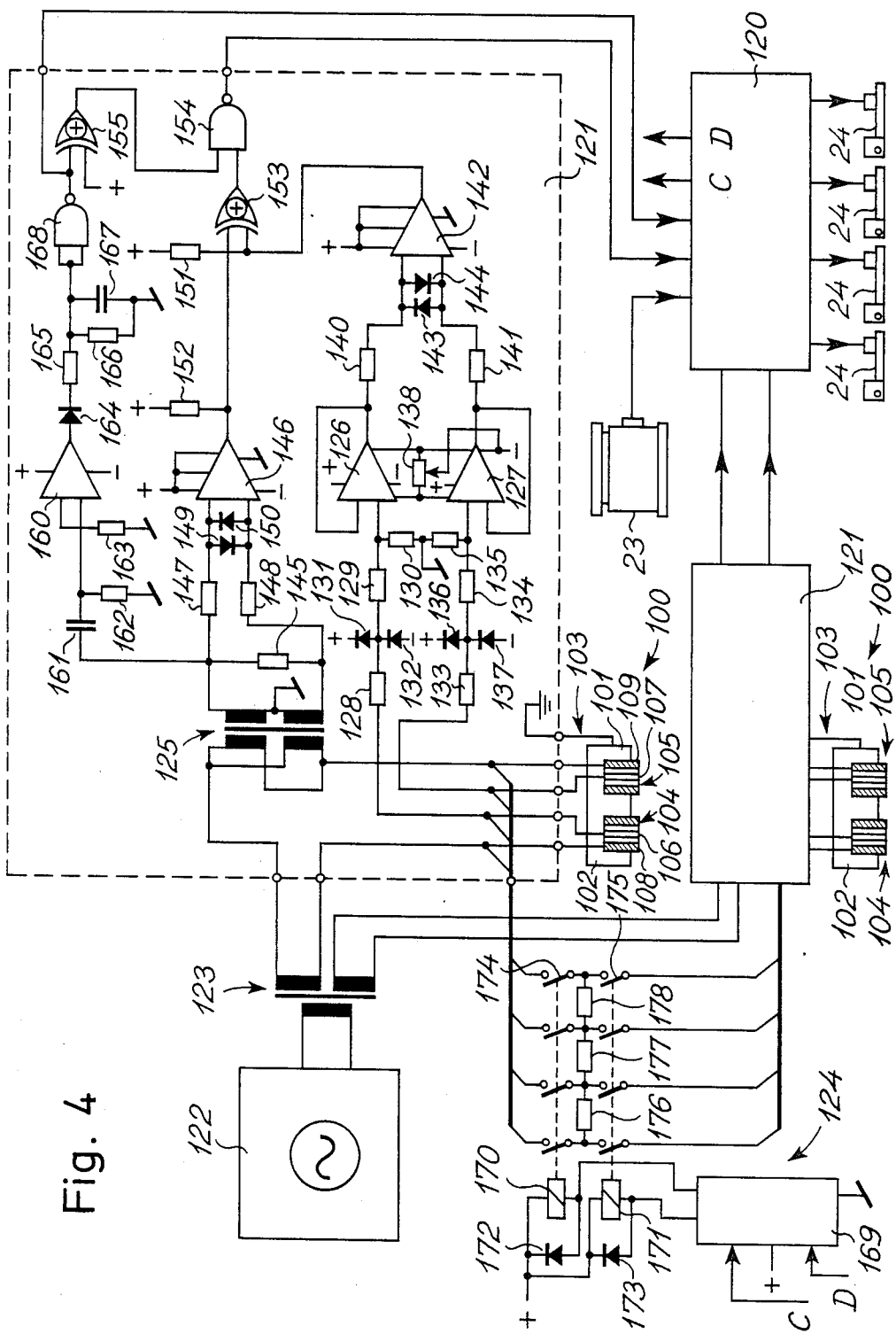
FIG. 4 is a diagram illustrating the electronic circuits of the apparatus.

FIG. 4 discloses a preferred embodiment of the electronic part of the apparatus including a central control means and electronic measuring amplifier means. The central control means is constituted by a microprocessor, which is indicated in FIG. 4 by a block 120. The microprocessor 120 is connected to the trap doors 24 and the weight or the weighing unit 23, which are controlled by the microprocessor and from which the microprocessor receives measuring signals, respectively, and two measuring amplifiers 121, which are identical to one another, and which are connected to a corresponding electrode assembly 100, and from which the measuring amplifier 121 in question receives measuring signals. In FIG. 4 one of the measuring amplifiers 121 are shown in detail, viz, the measuring amplifier which is defined by a dotted line while the other measuring amplifier 121 is shown schematically as a block defined by a solid line. Apart from the above described components, the electronic part or the electronic circuitry of the sorting apparatus comprises an oscillator 122, which is connected to the two measuring amplifiers 121 through a transformer 123 including a primary winding and two secondary windings, the primary winding of the transformer 123 being connected to the output of the oscillator 122 and the secondary windings of the transformer 123 being connected to each of the measuring amplifiers 121 and to a calibration and offset-compensation circuit 124. The signal supplied from the oscillator is preferably of a frequency of 2 kHz.

Each of the measuring amplifiers 121 serves the purpose of determining the phase angle between a current which is caused to run through the tissue of a fish and the voltage generated by the current across the impedance presented by the tissue of the fish in a manner described in the above mentioned report published by "Torry Research Station", Aberdeen, and further described in British patent specifications Nos. 1,262,749 and 1,287,190. The oscillator 122 causes the current to run through the transformer 123 from the graphite electrode 108 of the first electrode pair 104 through the tissue of the fish, which is in contact with the electrode assembly 100 and further through the graphite electrode 109 of the second electrode pair 105 and the primary windings of a connection transformer 125 and back to the oscillator 122 through the first mentioned transformer 123. The voltage is measured by means of the centre electrodes 106 and 107 of the electrode pairs 104 and 105, respectively, which are connected to the non-inverting input of an operational amplifier 126 and to the non-inverting input of an operational amplifier 127, respectively, through an appropriate input network. The operational amplifiers 126 and 127 are preferably constituted by operational amplifiers of high input impedance, typically of the order of 1.5 T$\Omega$ ($1.5 \times 10^{12} \Omega$), e.g. of the type comprising a mos-fet input circuit, e.g. an integrated operational amplifier of the type CA 3140. The said input networks of the operational amplifiers 126 and 127 are constituted by three resistors 128, 129, 130 and two diodes 131, 132 and three resistors 133, 134, 135 corresponding to the resistors 128, 129, 130 and two diodes 136, 137 corresponding to the diodes 131, 132, respectively. The input networks serve the purpose of providing a DC connection between the measuring electrodes, i.e. the centre electrodes 106 and 107, and the operational amplifiers serve the purpose of providing a short response time during measurement and further to protect the operational amplifiers 126 and 127 against voltages which numerically are larger than the supply voltages plus approximately 0.6 V (a single diode forward voltage drop). The operational amplifiers 126 and 127, which are connected in unity-gain mode further comprise a common potentiometer 138 serving the purpose of compensating for input offset voltages of the operational amplifiers. As will be seen from FIG. 4, the operational amplifiers 126 and 127 are supplied from a positive and a negative voltage supply source, which is preferably constituted by a symmetrical voltage supply, e.g. a voltage supply of $\pm 12$ V.

The outputs of the operational amplifiers 126 and 127 are connected to an inverting and a non-inverting input, respectively, of an operational amplifier 142, which is connected in high-gain mode through resistors 140, 141, respectively. Across the inputs of the operational amplifier 142, i.e. across the inverting and the non-inverting inputs of the operational amplifier, two oppositely directed diodes 143 and 144 are connected, which serve the purpose of limiting the voltages supplied from the operational amplifiers 126 and 127 to approximately $\pm 0.6$–$0.7$ V ($\pm$a single diode forward voltage drop) and provide a peak limited, i.e. a square wave signal, which is supplied to the operational amplifier 142, which, consequently, at its output supplies a square wave voltage of a frequency identical to the frequency of the voltage generated across the centre electrodes 106 and 107, the neutral passages of the square wave voltage corresponding to the neutral passages of said voltage.

The above mentioned alternating current which is induced or caused to run through the tissue of the fish in question produces a voltage across a resistor 145, which is connected to the secondary winding of said connection transformer 125. The voltage drop across the resistor 145 is detected by means of an operational amplifier 146 corresponding to the operational amplifier 142 and comprising resistors 147 and 148 corresponding to the resistors 140 and 141, respectively, and diodes 149 and 150 corresponding to the diodes 143 and 144, respectively. As will be understood, the operational amplifier 146 produces a square wave voltage at its output the frequency of which is identical to the frequency of the voltage generated across the resistor 145 and consequently identical to the frequency of the current, which is conducted through the tissue of the fish in question, and the neutral passages of which correspond to the neutral passages of the current. The outputs of the operational amplifiers 142 and 146 are connected to a respective input of an EXCLUSIVE-OR-gate 153 through appropriate biassing resistors 151 and 152, respectively, the output of the EXCLUSIVE-OR-gate 153 being connected to a first input of a NAND-gate 154. A second input of the NAND-gate 154 is connected to the output of a further EXCLUSIVE-OR-gate 155, which will be described in greater detail below.

Apart from the above described voltage and current detecting circuits, the measuring amplifiers 121 include a detector circuit, which serves the purpose of detecting whether a fish is in contact with the corresponding electrode assembly. The detector circuit is connected to one of the terminals of the resistor 145, across which a balanced voltage oscillation is generated by the above mentioned alternating current as will be seen from FIG. 4 in relation to the ground of the measuring circuit due to the connection transformer 125. The detector circuit includes an operational amplifier 160, the non-inverting input of which is connected to the said terminal of the resistor 145 through an input capacitor 161. To the above-mentioned non-inverting input of the operational amplifier 160 and to the invertinginput of the operational amplifier 160 grounding resistors 162 and 163, respectively, are connected. The operational amplifier 160, which is connected in high-gain mode, has its output connected to a half-wave rectifier and peak value detector circuit comprising a diode 164, two resistors 165 and 166, and a capacitor 167. The half-wave rectifier and peak value detector circuit is connected to an inverter, which is constituted by a NAND-gate 168, the two inputs of which are connected to the output of the half-wave rectifier and peak value detector circuit. The output of the NAND-gate 168 is, as will be seen from FIG. 4, connected to a control input of the microprocessor 120 and further to one of the inputs of the above mentioned EXCLUSIVE-OR-gate 155, the other input of which is connected to the positive voltage supply terminal, and which consequently also functions as an inverter.

The above described calibration and offset-compensation circuit 124, which is shown in the lower left-hand corner of FIG. 4, comprises a dual gate circuit 169, which is addressed from addressing outputs C and D, respectively, of the microprocessor 120 corresponding to the measuring amplifier 121, shown in the upper part of FIG. 4, and the measuring amplifier 121, shown in the lower part of FIG. 4, respectively. By supplying a control voltage from the control output C or from the control output D of the microprocessor 120, the dual gate circuit 169 activates a relay 170 and a relay 171, respectively. Across the relays 170 and 171, diodes 172 and 173, respectively, are connected, which serve the purpose of extinguishing induction currents in the corresponding windings of the corresponding relays. By activation, the relay 170 switches a pair of switches 174, whereas by activation the relay 171 switches a pair of switches 175, which connect three resistors 176, 177 and 178, as is illustrated in FIG. 4, across the electrodes of the corresponding electrode assembly, the resistor 176 being connected across the electrodes of the electrode pair 104, the resistor 177 being connected across the centre electrodes 106 and 107 of the electrode pairs 104 and 105, respectively, and the resistor 178 being connected across the electrodes of the electrode pair 105.

The circuit shown in FIG. 4 functions in the folowing manner, initially, i.e. before a fish is arranged in contact with the electrodes of an electrode assembly, the switches 174 and 175 are in the positions shown in FIG. 4, i.e. the calibration resistors 176, 177, 178 are not connected across any of the electrodes of the electrode assemblies. When a fish is brought into contact with an electrode assembly, i.e. the electrode assembly which is connected to the measuring amplifier shown in greater detail the current circuit or current half between the graphite electrodes 108 and 109 of the electrode pairs 104 and 105, respectively, is established, which results in a voltage drop across the resistor 145. The voltage drop is detected by the detector circuit including the operational amplifier 160 and the inverter 168, the output of which shifts from high to low. The control input of the microprocessor 120, which is connected to the output of the inverter 168, is consequently shifted to low, which corresponds to the detection of a fish in contact with the corresponding electrode assembly. The output of the EXCLUSIVE-OR-gate 155 is simultaneously shifted from low to high. Thereafter, the measuring amplifier is ready to supply measuring pulses from the output of the NAND-gate 154 to the microprocessor 120. The start of the operation of the sorting apparatus and at any other time, at which a calibration of the apparatus is desirable, the microprocessor 120 addresses the relay 170 through the C-output so as to connect the resistors 176, 177, 178 across the corresponding electrode assembly 100 in order to calibrate the measuring amplifier circuit.

The measurement of the phase angle between current and voltage is effected by the EXCLUSIVE-OR-gate 153 shifting its output to high, when the operational amplifiers 142 and 146 supply signals of different logical levels corresponding to a phase difference between current and voltage. When the output of the EXCLUSIVE-OR-gate 153 is high, and the output of the EXCLUSIVE-OR-gate 155 is also high, the NAND-gate 154 shifts to low, which corresponds to the presence of a phase difference between current and voltage. While the output of the NAND-gate 154 is low, the basic phase difference or phase angle measurement is carried out in the microprocessor 120. Since the frequency of the signal supplied from the oscillator 122 is a fixed frequency, the time difference between current and voltage constitutes a measure of the phase angle.

After the conclusion of the determination of the degree of freshness of the fish at one side of the fish by means of the first measuring assembly 100 and the corresponding measuring amplifier 121, the result of the measurement is stored in the microprocessor 120, and as described above with reference to FIG. 1 the fish is transferred in the continuous operation of the sorting apparatus to a weighing unit 23, which supplies a signal representing the weight of the fish in question to the microprocessor 120, in which the signal representing the weight is stored, and, thereafter, the degree of freshness of the fish at its other side is determined by means of the other measuring assembly and the corresponding measuring amplifier 121, and the result of the second determination is also stored in the microprocessor 120. On the basis of the measurements or determinations of the degrees of freshness and further on the basis of the signal representing the weight, the microprocessor 120 determines which one of the trap doors 24 is to be addressed and addresses the trap door in question.

It should be understood that various changes and modifications of the embodiments described above with reference to the drawings could be made within the scope of the present invention. As an example, the function of the trap doors 24 may be controlled in any other suitable manner than the one shown in the drawings and described above, and the sorting may be based on other criteria than freshness and weight. It is also possible to perform the sorting on the basis of freshness exclusively, and in that case the apparatus needs only a single trap door. In that case the apparatus may, for example, form part of a conveyor system by means of which the fish 19 or the pieces of food are transported to a processing station. In this manner it may be ensured that only completely fresh goods are processed further.

I claim:

1. A method of determining freshness of pieces of food based on electrical characteristics of the food, said method comprising:
   (a) successively moving said pieces of food along a first path of movement past a first set of electrodes and slidably contacting a first side of each piece of food with the first set of electrodes while it passes the same;
   (b) carrying out a plurality of successive first measurements by means of the first set of electrodes on the first side of each piece of food passing the first set of electrodes and slidably contacting same;
   (c) successively moving said pieces of food along a second path of movement past a second set of electrodes and slidably contacting a second side of each piece of food with said second set of electrodes while it passes the same;
   (d) carrying out a plurality of successive second measurements by means of said second set of electrodes on said second side of each piece of food passing the second set of electrodes and slidably contacting same; and,
   (e) determining a degree of freshness of each piece of food from such first and second measurements.

2. A method according to claim 1, wherein the degree of freshness of each piece of food is determined by averaging said pluralities of first and second measurements.

3. A method according to claim 2, wherein said pieces of food are pieces of meat.

4. A method according to claim 1, wherein the degree of freshness of each piece of food is based on measurements of an electrical characteristic selected from a group consisting of electrical impedance, phase angle, resistance, reactance, sharpness of resonance, and time constant.

5. A method according to claim 4, wherein said pieces of food are pieces of meat.

6. A method of determining freshness of pieces of food based on electrical characteristics of the food, said method comprising:
   (a) successively moving said pieces of food along a first path of movement past a first set of electrodes comprising a first pair of emitter electrodes and a second pair of receiver electrodes, and slidably contacting a first side of each piece of food with the first set of electrodes while it passes the same;
   (b) carrying out of plurality of successive first measurements by means of the first set of electrodes on the first side of each piece of food passing the electrodes and slidably contacting same, each measurement comprising supplying an alternating current to said pair of emitter electrodes, measuring an alternating voltage generated across said pair of receiver electrodes, and measuring the phase angle between the current supplied and the voltage generated; and,
   (c) determining a degree of freshness of each piece of food from such measurements.

7. A method according to claim 6, wherein the degree of freshness of each piece of food is determined by averaging said plurality of measurements.

8. A method according to claim 6, further comprising:
   (a) successively moving said pieces of food along a second path of movement past a second set of electrodes and slidably contacting a second side of each piece of food with said second set of electrodes, while it passes the same;
   (b) carrying out a plurality of successive second measurements by means of said second set of electrodes on said second side of each piece of food passing the second set of electrodes and slidably contacting same; and,
   (c) determining the degree of freshness of each piece of food from such first and second measurements.

9. A method according to claim 6, wherein said pieces of food are pieces of meat.

10. An apparatus for determining freshness of pieces of food, said apparatus comprising:
    (a) a supporting surface;
    (b) moving means for successively moving the pieces of food along a path of movement defined by said supporting surface;
    (c) measuring means for measuring characteristics of the pieces of food and for determining a degree of freshness therefrom, said measuring means comprising first and second sets of electrodes positioned at the supporting surface along the path of movement to engage with and carry out a plurality of measurements upon sliding contact with each of said pieces of food;
    (d) turning means positioned between said first and second sets of electrodes for turning upside-down passing pieces of food; and,
    (e) sorting means for sorting the pieces of food on the basis of the measurements carried out by the measuring means.

11. An apparatus according to claim 10, wherein at least one set of said first and second sets of electrodes projects from the supporting surface.

12. An apparatus according to claim 10, wherein the supporting surface comprises a pair of vertically spaced upper and lower, substantially horizontally extending surface parts, and wherein the moving means comprises an endless conveyor belt which is provided with carriers and has upper and lower runs extending along the upper and lower surface parts, respectively.

13. An apparatus according to claim 11, wherein said measuring means comprises an electronic measuring amplifier means which is connected to at least one of said first and second sets of electrodes for measuring an electrical characteristic selected from a group consisting of electrical impedance, phase angle, resistance, reactance, sharpness of resonance, and time constant.

14. An apparatus for determining freshness of pieces of food, said apparatus comprising:
    (a) a supporting surface;

(b) moving means for successively moving the pieces of food along a path of movement defined by said supporting surface;
(c) measuring means for measuring characteristics of the pieces of food and for determining a degree of freshness therefrom, said measuring means comprising a first set of electrodes projecting from the supporting surface and oriented to slidably engage a piece of food moved across said supporting surface, for conduction of a plurality of measurements thereon; and,
(d) sorting means for sorting the pieces of food on the basis of the measurements carried out by the measuring means.

15. An apparatus according to claim 14, wherein said measuring means further comprises a second set of electrodes positioned at the supporting surface along the path of movement to engage with each of said pieces of food, said apparatus further comprising turning means positioned between said first and second sets of electrodes for turning upside-down passing pieces of food.

* * * * *

UNITED STATES PATENT AND TRADEMARK OFFICE
CERTIFICATE OF CORRECTION

PATENT NO.  : 4,758,778
DATED       : July 19, 1988
INVENTOR(S) : Bjorn Kristinsson It is certified that error appears in the above-identified patent and that said Letters Patent is hereby corrected as shown below:

Title page, Col. 1, [56] References cited, FOREIGN PATENT DOCUMENTS 74463 7/1962 Denmark, should be 109,112 7/1962 Denmark 421308 12/1966 Denmark, should be 106,165 12/1966 Denmark 92107 1/1958 Netherlands, should be 92107 1/1958 Norway Col. 1, line 62 --"copmrises"-- should be --comprises--

Signed and Sealed this

Fifteenth Day of May, 1990

*Attest:*

HARRY F. MANBECK, JR.

*Attesting Officer*                *Commissioner of Patents and Trademarks*